United States Patent [19]

Holmsen et al.

[11] 4,266,964

[45] May 12, 1981

[54] HERBICIDE ANTIDOTE COMPOUNDS AND METHOD OF USE

[75] Inventors: Theodore W. Holmsen, Clayton; Norman H. Kurihara, Walnut Creek, both of Calif.; Paul A. Thomas, Shawnee Mission, Kans.

[73] Assignee: The Dow Chemical Company, Midland, Mich.

[21] Appl. No.: 34,891

[22] Filed: Apr. 30, 1979

[51] Int. Cl.$^3$ ............................................. A01N 25/32
[52] U.S. Cl. .......................................... 71/94; 71/88; 71/100
[58] Field of Search ...................................... 71/94, 88

[56] References Cited

U.S. PATENT DOCUMENTS

| | | | |
|---|---|---|---|
| 3,135,594 | 6/1964 | Goring | 71/11 |
| 3,224,950 | 12/1965 | Johnston et al. | 264/158 |
| 3,296,272 | 1/1967 | Johnston | 260/294.8 |
| 3,418,323 | 12/1968 | Johnston et al. | 260/290 |
| 3,420,833 | 1/1969 | Taplin | 260/283 |
| 3,424,754 | 1/1969 | Taplin | 260/290 |
| 3,682,936 | 8/1972 | Torba | 260/297 R |
| 4,124,376 | 11/1978 | Pallos et al. | 71/118 |

FOREIGN PATENT DOCUMENTS 828587 4/1975 Belgium.
1469741 4/1977 United Kingdom.

OTHER PUBLICATIONS

Harrison Proceedings of the Beltwide Cotton Production Mechanization Conf. 1-1978 p. 82.
Herbicide Handbook of the Weed Society of America, 3rd Edition, 1974, Champaign, Illinois, pp. 77-80, 110-113, 179-181, 252-255, 296-299 and 412-415.

*Primary Examiner*—Catherine L. Mills

[57] ABSTRACT

Crop tolerance to thiocarbamate herbicides, such as EPTC and butylate, and to the herbicide 2-(2,-2,2-trichloroethyl)-2-(3,5-dichlorophenyl)oxirane is improved on applying to the locus of the crop at least an antidotal amount of a chloropyridine having a chloromethyl, dicloromethyl or trichloromethyl group on the ring and at least one additional ring substituent which may be Cl, $NH_2$, $CCl_3$, methylsulfonyl or morpholino. The herbicide and antidote compounds may be applied concurrently separately or as a composition containing both compounds in combination.

28 Claims, No Drawings

HERBICIDE ANTIDOTE COMPOUNDS AND METHOD OF USE

BACKGROUND OF THE INVENTION

1. Field of the Invention

The invention relates to the use of specified chloromethyl chloropyridines as antidotes or safeners for the protection of valuable crops from unwanted herbicidal action or stress on the crops upon the application of a thiocarbamate herbicide such as S-ethyl diisobutylthiocarbamate or S-ethyl dipropylthiocarbamate or the herbicide 2-(2,2,2-trichloroethyl)-2-(3,5-dichlorophenyl)oxirane applied to the locus of the valuable crops and to a herbicidal composition containing at least one of said chloromethylchloropyridines and one of the referenced herbicides.

2. Description of Prior Art

The known herbicide compounds exhibit a spectrum of activity against various weed species and crops. The extent of herbicidal action varies from plant species to plant species and a dosage rate of herbicidal compound which is tolerated by a given valuable crop may not be sufficient to permit control of each of the weed species that are usually encountered in growing the specified crop. Sometimes a combination of two or more herbicide compounds will provide an improved spectrum of weed control without exceeding good crop tolerance.

Another approach to facilitating broad spectrum weed control without exceeding crop tolerance is to employ an antidote or safener compound which selectively improves the tolerance of one or more valuable crops without substantially diminishing the herbicidal action of the herbicidal compound against the weed species it is desired to control.

Butylate, i.e., S-ethyl diisobutylthiocarbamate is a well-known herbicide active against some of the annual and perennial grassy weeds as well as some of the broad leaf weeds in the presence of crops such as sweet corn, field corn and cotton, as described in Herbicide Handbook of the Weed Science Society of America, Third Edition, Weed Science Society of America, Champaign, Ill., 1974 at page 77.

EPTC, i.e., S-ethyl dipropylthiocarbamate is a well-known herbicide used for the control of some of the annual grassy weeds as well as some of the broad leaf weeds in the presence of crops such as alfalfa, garden produce, citrus corn and cotton crops. EPTC is further described starting at page 179 of the referenced Herbicide Handbook.

Molinate, i.e., S-ethyl hexahydro-1H-azepine-1-carbothioate, is a well-known herbicide active against some of the annual grassy weeds and broadleaf weeds in the presence of crops, particularly rice, as described in said Herbicide Handbook.

Vernolate, i.e., S-propyl dipropylthiocarbamate, is a well-known herbicide active against some of the annual grassy weeds and broadleaf weeds in the presence of crops such as soybeans, peanuts, tobacco and sweet potatoes, as described in said Herbicide Handbook.

Cycloate, i.e., S-ethyl cyclohexylethylthiocarbamate, is a well-known herbicide used for the control of some annual grassy weeds and broadleaf weeds in the presence of crops such as sugarbeets, spinach and table beets, as described in said Herbicide Handbook.

Pebulate, also referred to as PEBC, i.e., S-propyl butylethylthiocarbamate, is a well-known herbicide useful for the control of some grassy weeds and broadleaf weeds in the presence of crops such as sugarbeets, tomatoes and tobacco, as described in said Herbicide Handbook.

Each of the thiocarbamate herbicides described, which are representative of the S-alkyl, dialkylthiocarbamates wherein alkyl contains 2 to 6 carbon atoms and is straight chained, branched or cyclic, have an upper dosage limit when applied to valuable crops. In the case of butylate, a commercially sold composition of the herbicide contains the antidotal compound N,N-diallyl-2,2-dichloroacetamide, also commonly known as R-25788, which safens the action of the butylate toward corn, e.g., substantially without affecting its herbicidal properties against weed species, permitting the use of a somewhat higher, more effective, dosage rate. This antidotal compound also safens the other thiocarbamates towards valuable crops which show at least some tolerance to these herbicides.

2-(2,2,2-Trichloroethyl)-2-(3,5-dichlorophenyl)oxirane is a herbicide active against annual grassy weeds. Such compound is described in Canadian Patent 1,040,642 and British Patent 1,469,741. This oxirane compound is prepared by epoxidation of 2-(3,5-dichlorophenyl)-(4,4,4-trichloro)-butene-1 with a percarboxylic acid, e.g., peracetic acid, preferably in the presence of a buffer solution of the acid reactant, e.g., sodium acetate with peracetic acid. In carrying out the reaction the chlorophenyl substituted butene is usually blended with a solvent medium such as methylene chloride or 1,2-dichlorobenzene and mixed slowly with the percarboxylic acid-buffer solution. A suitable ratio of reactants is in the range of one mole of the butene compound to one to six moles of percarboxylic acid. Reaction proceeds rather slowly at a modest temperature of about 20° to 40° C. and ambient atmospheric pressure over a period of about 24 to 100 hours or more. The oxirane is recovered upon, e.g., washing the reaction mixture with water and neutralizing it with a base such as sodium carbonate, drying the oil over anhydrous sodium sulfate, and concentrating the residue under reduced pressure.

The use of nitrapyrin, i.e., 6-chloro-2-trichloromethylpyridine and related chloropyridines having a trichloromethyl substituent on the ring for the suppression of nitrification of ammonium nitrogen is described and claimed in U.S. Pat. No. 3,135,594. The preparation of such compounds or close analogs or isomers is described in U.S. Pat. Nos. 3,224,950; 3,296,272; 3,418,323; 3,420,833 and 3,424,754, the teachings of which are incorporated herein by reference. In general, preparation of these compounds involves high temperature chlorination of alpha-picoline, gamma-picoline, 2,6-dimethylpyridine, 2-chloromethylpyridine or aminochloropyridine in which the pyridine compound is contacted by gaseous chlorine at a temperature of about 100° to 165° C. until the requisite degree of chlorination is achieved in the ring or the side chain, and the resulting isomers, homologs or analogs separated.

A chloropyridine with an active chlorine in one of the 2 or the 4 position and a chloromethyl group in the other of the 2 or 4 positions is reacted with a nitrogen base such as ammonia or an aliphatic acyclic or heterocyclic amine, usually with an amount of the base in excess of the stoichiometric amount, and at a temperature of about 80° to 110° C. for about 30 to 120 minutes, after which the reaction mixture is allowed to cool and the desired product is recovered by extracting or washing out the unreacted base with water.

Alkylthiochloropyridines or alkylthiochloro-chloromethylpyridines are prepared by reacting an alkali metal mercaptan with a 4-chloropyridine or 4-chloro-chloromethylpyridine at a temperature of about 60° to 100° C. The alkylthiochloropyridine or alkylthio-chloro-chloromethylpyridine compounds are converted to the corresponding sulfonyl compounds by oxidation with fuming nitric acid, nitric acid, hydrogen peroxide, potassium permanganate or a mixture of alkali metal chromate and sulfuric acid. Generally a temperature of about 15° to 120° C. suffices though the use of either hydrogen peroxide or nitric acid as oxidizing agent requires a higher minimum reaction temperature of the order of 75° or 80° C.

SUMMARY OF THE INVENTION

Plant crops are at least partially protected from injury due to an active herbicidal compound selected from the group consisting of the S-alkyl, dialkylthiocarbamates, wherein alkyl contains 2 to about 6 carbon atoms and is straight chained, branched or cyclic, such as, S-ethyl diisobutylthiocarbamate, S-ethyl dipropylthiocarbamate, and 2-(2,2,2-trichloroethyl)-2-(3,5-dichlorophenyl) oxirane upon applying to the soil in which a herbicidally effective amount of said active herbicidal compound is used a non-phytotoxic antidotally effective amount of an antidote compound corresponding to the formula:

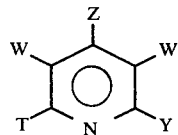

wherein:
T is H, Cl, CCl$_3$, CH$_2$Cl or CHCl$_2$;
Y is H, NH$_2$, Cl, CCl$_3$, CHCl$_2$ or CH$_2$Cl;
Z is H, Cl, CCl$_3$, —SO$_2$CH$_3$ or morpholinyl;
each W is independently H or Cl; and at least one of T, Y and Z is chloromethyl and at least one of T, W, Y and Z is Cl;
said chloropyridine compound being antidotally active with said herbicide compound and wherein said chloropyridine compound is present in an effective amount ranging between about 0.01 to about 4 parts by weight of the chloropyridine compound per part of herbicide compound. Preferably the pyridine compound does not have more than four ring substituents.

In addition, the safening action of N,N-diallyl-2,2-dichloroacetamide in the presence of the thiocarbamate herbicides is increased towards valuable crops by employing an antidotally effective amount of the present chloromethyl chloropyridine compound in combination or applied substantially concurrently.

A herbicidal composition comprising an active herbicide compound selected from the above mentioned herbicides and a nonphytotoxic antidotally effective amount of one or a mixture of the said chloromethyl chloropyridine compounds is useful in the control of undesired vegetation in the locus of a valuable crop whereby stress due to the use of the herbicide compound is reduced for the valuable crop. The invention also contemplates a mixture of 2,2-dichloro-N,N-diallylacetamide in antidotal amounts with the foregoing composition.

More Detailed Description of the Invention

For the purpose of the following description and the appended claims an antidotally effective amount of one of the present chloromethyl chloropyridine compounds is that amount which significantly reduces the stress of the thiocarbamate herbicide or oxirane herbicide on the valuable crop being treated. The reduction in stress, or safening effect, is ordinarily visibly observed as at least a significant reduction or elimination of shortened crop plant growth because of the herbicide, or of malformation of the leaves of the crop plant, though the reduction in stress may be evidenced only in increased crop yields when the herbicide stress is present, but too slight to cause visibly shortened plants or malformed leaves.

The term chloromethyl as used herein is meant to embrace monochloromethyl and dichloromethyl in addition to trichloromethyl unless specifically stated otherwise.

It has now been discovered that crop plants can be protected against injury by the described herbicidal compounds alone or mixed with other herbicides or fungicides and/or the tolerance of the plants can be substantially increased to the herbicide compounds by adding to the soil in the locus of the crop plants an antidote compound of the class described herein, the herbicide and antidote being added as a combination composition or separately at respective times, but close enough in time to substantially avoid unwanted stress upon rops wherein the herbicide compounds are utilized either preemergently or postemergently. Thus the safener can be added to the soil from slightly before to slightly after the introduction of the herbicide.

Specific examples of suitable chloropyridines having a chloromethyl group on the ring include nitrapyrin, i.e., 6-chloro-2-trichloromethyl pyridine, 2,4-dichloro-6-dichloromethyl pyridine, 2-chloromethyl-3,4,5-trichloropyridine, 2-chloro-4-methylsulfonyl-6-trichloromethyl pyridine, 2,6-dichloro-4-trichloromethyl pyridine, 4-chloro-2,6-(bis-trichloromethyl) pyridine, 2-amino-6-chloro-4-trichloromethyl pyridine and 3,5-dichloro-4-morpholino-2-trichloromethyl pyridine. These are compounds of moderate boiling point that are readily soluble in many common organic solvents such as xylene or acetone or petroleum distillates and are readily dispersed in water with the use of most any of the common surface-active agents.

The significant volume crops protected in the case of the thiocarbamates are primarily corn, cotton, soybeans, navy beans and other dry beans and legumes, peanuts, rice and sugar beets. In the case of the oxirane compound the crops are primarily corn, sorghum, rice and sobyeans.

The most significant weeds to be controlled by these herbicides in these crops are crabgrass, Johnson grass, foxtail and barnyard grass, in addition to other grassy weeds and many small seeded broadleaf weeds.

The thiocarbamates and the oxirane herbicide are ordinarily incorporated into the soil in pre-plant, i.e., preemergence applications, or subsequently in early postemergence operations. The instant antidotes, or safeners, are readily mixed with the herbicides in emulsifiable concentrates, or flowable suspensions where appropriate, or wettable powders or in granules and sprayed or broadcast upon the seed bed and promptly incorporated into the soil because of the relative volatility of the safener compound as well as of the thiocarbamates. The herbicides and the safener may also be applied in band applications, for example, as a part of the seed planting operation or in side dressing type applications made early postemergence.

In addition the present type of safener compound may also be applied in greatly diluted form in irrigation water supplied to the seed bed just before or just after applying the herbicide in other operations, e.g. in a concentration as low as 0.00001 percent by weight.

The concentration of the chloromethyl-chloropyridine compound in compositions to be employed for the treatment of growth media, i.e., the soil, is not critical and may vary considerably provided the required dosage of safener is supplied to the growth media. The concentration of chloromethyl chloropyridine compound may vary from about 0.00001 percent by weight to about 95 percent by weight of the composition, depending on whether the composition is a treating composition, such as a tank mix, or a concentrate composition and whether it is in the form of a solid or a liquid. In aqueous liquid treating compositions, a concentration of from about 0.01 to about 5 percent is preferred, while a concentration in the range of about 0.125 percent to about 2.5 percent by weight is more preferred. However, if the safener is applied in combination with one of the recited thiocarbamate or oxirane herbicides it should be present in the mixture at a weight ratio to the herbicide in the range of about 1 part of safener to from about 0.5 to 50 parts of herbicide, preferably about 0.5 to about 10 parts of herbicide and most more preferably about 0.5 to about 6 parts of herbicide, and the mixture should contain sufficient emulsifying agent to provide for emulsification of the components in water, if present in the concentrate, or at least subsequently in any aqueous treating composition preferred therefrom. In addition, the composition should contain an inert agricultural carrier, such as water, an organic solvent, or a suitably clay as used in preparing conventional wettable powders.

A useful composition for simultaneous application of herbicide and safener is made up by dispersing or emulsifying, with an emulsifier, both components in an aqueous fertilizer solution such as URAN 32 brand liquid fertilizer containing 32 percent by weight nitrogen. Such composition is made up to supply the requisite amount of herbicide, usually about 1 to about 6 pounds per acre, and about 1 to about 2 pounds per acre of safener, in most cases, in about 20 to 50 gallons of liquid, sprayable composition, as many growers are equipped to apply liquid compositions at about that rate. A preferred aqueous treating composition then contains, by weight, from about 0.25 to about 1.25 percent of the safener and from about 0.25 to about 3.75 percent of thiocarbamate or oxirane herbicide, in addition to the requisite emulsifier component, and, an inert carrier liquid, such as water, or water and a minor amount of organic solvent used in making up an emulsifiable concentrate as is well understood in the herbicide formulation art.

The safener may also be applied separately in liquid ammonia in the manner in which nitrapyrin is currently being applied in regular agronomic practice. The thiocarbamate and chloropyridine safener may be applied concurrently as an aqueous composition following current agronomic practices for application of the thiocarbamates alone.

Butylate is currently being sold commercially with an added safener, R-25788, referred to above. This safener is beneficially used with any of the thiocarbamates at a rate, by weight, of about ⅛ to 1 part R-25788 to 12 parts thiocarbamate, preferably about 1 part R-25788 in field applications. It has also now been discovered that use of the present safener further reduces the stress of the thiocarbamates towards valuable crops substantially without reducing the herbicidal action towards noxious weeds, such as the grassy weeds and fine seeded broadleaf weeds.

Thus, another preferred embodiment of the invention contemplates a treating composition containing about 0.25 to about 3.75 percent of a thiocarbamate herbicide plus about 0.25 to 0.63 percent of R-25788 and about 0.25 to about 1.25 percent of the present safener, and the balance water and emulsifier and any fertilizer and fungicide and additional compatible herbicide components desired.

When applied alone, the safener may be applied in any of the ways described for nitrapyrin in U.S. Pat. No. 3,135,594, the disclosure of which is incorporated by reference. Thus, the safener may be applied as a solution or dispersion in liquid ammonia, or in water or aqueous composition, or as a wettable powder or as a dust or granule.

Liquid compositions containing the desired amount of chloro-chloromethylpyridine safener compound alone or in combination with the thiocarbamate herbicide or oxirane herbicide, with or without R-25788 additionally or also with or without one or more compatible herbicides not injurious to the crop to be treated, may be prepared by dispersing the latter in one or more liquid carriers such as water or an organic solvent, with or without the aid of a suitable surface-active dispersing agent or emulsifying agent. Suitable organic solvents include acetone, diisobutylketone, methanol, ethanol, isopropyl alcohol, toluene, methylene chloride, chlorobenzene and the petroleum distillates. The preferred organic solvents are those which are of such volatility that they leave little permanent residue in the soil. When the solutions of the pyridine compound with or without other components in organic solvents are to be further diluted to produce aqueous dispersions, the preferred solvents include acetone and the alcohols. When the liquid carrier is entirely organic in nature, particularly desirable carriers are the petroleum distillates boiling almost entirely under 400° F. at atmospheric pressure and having a flash point above about 80° F. Dispersing and emulsifying agents which may be employed in liquid compositions include condensation products of alkylene oxides with phenols and organic acids, alkyl aryl sulfonates, polyoxyalkylene derivatives of sorbitan esters, complex ether alcohols, mahogany soaps and the like. The surface-active agents are generally employed in the amount of from 1 to 20 percent by weight of the combined weight of the pyridine compound and any herbicide present.

EXAMPLE 1—Nitrapyrin as an Antidote for EPTC on Cotton

Four-inch round pots were filled to within about 2 cm of the top with a good loam soil (50% sand, 34% silt, 16% clay with 0.8% organic carbon). Cotton seeds (*Gossypium hirsutium var. Acala SJ2*) were placed on the soil surface in each pot and covered with about 2 mm of soil. The soil surface of some of the pots was sprayed with an aqueous solution of test chemical while pots serving as controls received no such spray. In each case another 7 mm of soil was added promptly and tamped. The aqueous solution in some cases contained EPTC, i.e., S-ethyl dipropylthiocarbamate; in other cases nitrapyrin, and in other cases both EPTC and nitrapyrin. When used, the carbamate herbicide compound was applied at respective rates of 2, 1 and 0.5 lb per acre, while the nitrapyrin was applied at the rate of 1 lb per acre. In each case, the composition of aqueous solution was made up at such a concentration that 20 gallons of the solution would provide the stated dose for one acre of seed bed. Under these circumstances the weight by weight concentration of safener or herbicide in the solution is as follows:

| Lbs/acre | Wt. % |
|---|---|
| 0.5 | 0.31 |
| 1 | 0.625 |
| 2 | 1.25 |
| 4 | 2.5 |

All the pots were watered and maintained in a greenhouse for growth under prevailing conditions conducive to growth (temperature 65°–85° F.; natural daylight supplemented to 14 hours with metal halide lamps). The plants were harvested 19 days after seeding by cutting the stems at the soil level. The above ground plant parts or tops from respective pots were each dried at 95° C. for 24 hours and weighed. There were three replicates (pots) of four plants each for each test run. The average results for the respective sets of replicates are tabulated as follows in Table I.

TABLE I

| EPTC Lb/Acre | Evaluation of Nitrapyrin as Antidote Average Wt. of 4 Plants, gms. | |
|---|---|---|
| | No nitrapyrin | 1 Lb/Acre Nitrapyrin |
| 0 | 1.50 | 1.60 |
| 0.5 | 0.87 | 1.18 |
| 1 | 0.79 | 1.04 |
| 2 | 0.40 | 0.50 |

These results show that nitrapyrin when applied alone has only a slight effect on the growth of seedling cotton plants under the conditions of this test. However, when the cotton seedlings were stressed with the carbamate herbicide applied at rates in the range of 0.5 to 2 lb/acre the application of nitrapyrin at the rate of 1 lb/acre provided for a 20 to 36 percent increase (improvement) in the growth of the cotton plants.

EXAMPLE 2—Nitrapyrin as an Antidote for EPTC on Corn

A test was carried out as in Example 1 except that corn (Zea mays cv. Pioneer 3048) was used instead of cotton, there were three plants per pot and EPTC was also applied at the rate of 4 lbs/acre with and without nitrapyrin. The plant tops were again cut, dried and weighed and the results tabulated on Table II.

TABLE II

| EPTC Lbs/Acre | Evaluation of Nitrapyrin as an Antidote Average Wt. of 3 Plants, gm. | |
|---|---|---|
| | No Nitrapyrin | 1 Lb/Acre Nitrapyrin |
| 0 | 1.94 | 1.90 |
| 0.5 | 1.80 | 2.02 |
| 1 | 1.28 | 1.60 |
| 2 | 0.83 | 0.94 |
| 4 | 0.29 | 0.65 |

The results of this test show that under the conditions employed, nitrapyrin did not improve the growth of corn seedling plants in the absence of EPTC, but nonetheless the nitrapyrin added provided for increased plant growth in the range of about 12 to about 124 percent over that observed with EPTC present, but no nitrapyrin.

EXAMPLE 3—Nitrapyrin as an Antidote for Oxirane Compound on Corn

A test was carried out as in Example 2 except that 2-(2,2,2-trichloroethyl)-3,5-dichlorophenyl oxirane was used as the herbicide and there were six corn plants per pot. Again the tops were cut, dried and weighed and the results tabulated in Table III.

TABLE III

| *Oxirane Compound Lb/Acre | Evaluation of Nitrapyrin as an Antidote Average Wt. of 6 Plants, gms. | | |
|---|---|---|---|
| | No Nitrapyrin | Nitrapyrin Applied 1 Lb/Acre | 2 Lb/Acre |
| 0 | 3.06 | 2.83 | 3.20 |
| 2 | 2.48 | 3.03 | 2.65 |

*2-(2,2,2-trichloroethyl)-3,5-dichlorophenyl oxirane

These results show that the addition of nitrapyrin at each of 1 and 2 lbs/acre rates overcomes the growth reduction caused by the oxirane herbicide applied alone.

EXAMPLE 4—Nitrapyrin as an Antidote for Butylate on Corn

A test was carried out as in Example 3 except that the herbicide used was butylate applied at rates of 0, 3, 6 and 12 lbs/acre, nitrapyrin was applied at the rate of 0.5 lb/acre, four pots per respective treatment level, and all treatments were at the rate of 50 gallons per acre of solution which included 75% "URAN 32" liquid fertilizer and 0.17% "UNITE" compatibility agent, or emulsion stabilizer. At the conclusion of the brief growing period the plant tops were cut, dried and weighed as in the other tests and the results tabulated in Table IV.

TABLE IV

| Butylate Lb/Acre | Evaluation of Nitrapyrin As An Antidote Average Wt. of 6 Plants, gm. | |
|---|---|---|
| | No Nitrapyrin | 5 Lb/Acre Nitrapyrin |
| 0 | 1.69 | 1.69 |
| 3 | 1.39 | 1.79 |
| 6 | 0.95 | 1.26 |
| 12 | 0.79 | 0.95 |

The results of the foregoing test show that improvements in growth of corn of about 20 to 33 percent are observed on applying 0.5 lb/acre nitrapyrin along with butylate in the presence of a nitrogen fertilizer.

EXAMPLES 5–11—Substituted Chloropyridines As Antidotes for Butylate on Corn

In a series of tests carried out in substantially the same manner as the tests described in Example 4, butylate was applied at the rate of 6 lbs/acre in some of the pots, with and without various chloropyridine compounds at rates ranging from 0.125 to 2 lbs/acre. Nitrapyrin was also applied at the rate of 0.5 lb/acre along with butylate in other pots and some pots were left untreated. As the tests were conducted at various times, the nitrapyrin test was repeated and served as a positive control. For each treatment there were three replications of six corn plants each. The plant tops were cut as in the preceeding tests, but after various growing periods from planting to harvest, and then dried and weighed. The chloropyridines tested, application rates, the growing periods and test weights are summarized in the following TABLE V.

a 27 percent improvement when nitrapyrin was used to further safen the combination of butylate and R-25788.

EXAMPLE 14—Nitrapyrin as an Antidote for Butylate With and Without R-25788 on Grassy Weeds In a series of tests, the herbicide properties of butylate on the grassy weeds, crabgrass, Johnson grass and barnyard grass were determined for butylate applied alone, in combination with R-25788 and nitrapyrin, respectively, and in combination with both R-25788 and nitrapyrin at butylate rates of 12, 6 and 3 pounds per acre and nitrapyrin rates of 0.5 and 1 pounds per acre. No alteration of the herbicidal action of butylate was observed and all three grassy weeds were controlled in each test.

TABLE V
Evaluation of Other Chloropyridines as Antidotes

| Example | Growth Period Days | Test Compound | Antidote Rate Lb/A | Butylate | Compound + Butylate | Nitrapyrin + Butylate | Untreated Controls |
|---|---|---|---|---|---|---|---|
| 5 | 23 | 3,5-dichloro-4-morpholino-2-trichloromethylpyridine | 2 | 1.52 | 1.82 | 1.82 | 2.14 |
| 6 | 26 | 2-amino-6-chloro-4-trichloromethylpyridine | 0.125 | 1.90 | 2.58 | 2.48 | 2.80 |
| 7 | 26 | 2,6-(bis-trichloromethyl)-4-chloropyridine | 0.5 0.125 | 1.90 | 2.51 2.43 | 2.48 | 2.80 |
| 8 | 26 | 2,6-dichloro-4-trichloromethylpyridine | 0.125 | 1.90 | 2.43 | 2.48 | 2.80 |
| 9 | 28 | 2-chloro-4-methylsulfonyl-6-trichloromethylpyridine | 0.5 0.125 | 2.44 | 3.00 2.76 | 2.73 | 2.84 |
| 10 | 16 | 2-chloromethyl-3,4,5-trichloropyridine | 0.5 | 1.16 | 1.42 | 1.26 | 1.67 |
| 11 | 16 | 2,4-dichloro-6-dichloromethylpyridine | 2 | 1.16 | 1.40 | 1.26 | 1.67 |

The results show that the herbicidal stress of butylate on corn was significantly decreased by each test compound at the rates applied. The untreated controls are representative of results in greenhouse tests wherein there is no competitive pressure from weeds as would be the case of field grown crops.

EXAMPLES 12 and 13—Nitrapyrin as an Antidote for Butylate With and Without R-25788 on Corn A test was carried out substantially as in Example 4 with 4 pots per respective treatment and 6 plants per pot, but utilizing 1 lb. of nitrapyrin per 12.2 lbs of butylate and also duplicating each test by employing, in place of butylate alone, a combination of butylate and R-25788, utilizing 1 lb. thereof per 12.2 lbs. of butylate.

The $GR_{80}$ on corn values, i.e., dose rates of butylate to cause 80% reduction in growth of corn plants, were calculated from the dry plant weights measured, and the values tabulated as follows:

TABLE VI
Comparison of Safening of Butylate With and Without R-25788

| Herbicide Combination | $GR_{80}$ on Corn Lb/Acre |
|---|---|
| butylate | 2.25 |
| butylate + nitrapyrin | 2.61 |
| butylate + R-25788 | 5.00 |
| butylate + R-25788 + nitrapyrin | 6.35 |

The weight values in the table are for $GR_{80}$ of the butylate per se and not butylate and nitrapyrin weights combined.

The test results showed a 16 percent improvement in growth when nitrapyrin was used to safen butylate, and On repeating any of the foregoing tests utilizing the other thiocarbamates contemplated with any of the chloromethyl-chloropyridines within the scope of the present description and upon the crops herein described, substantially the same excellent safening affects are observed without noticeable diminution of herbicidal properties towards grassy weeds and small seeded broadleaf weeds.

Likewise on repeating the tests with any of the chloromethyl-chloropyridines and the oxirane herbicide upon the crops described substantially the same excellent safening is observed without noticable diminution of herbicidal properties towards grassy weeds.

We claim:
1. A herbicidal composition comprising an active herbicide compound selected from the group consisting of the herbicidal S-alkyl dialkylthiocarbamates wherein alkyl contains 2 to about 6 carbons and is straight chained, branched or cyclic and 2-(2,2,2-trichloroethyl)-2-(3,5-dichlorophenyl)oxirane and a nonphytotoxic antidotally effective amount of a chlorpyridine compound having the formula:

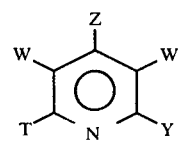

wherein:
T is H, Cl, $CCl_3$, $CH_2Cl$ or $CHCl_2$;
Y is H, $NH_2$, Cl, $CCl_3$, $CHCl_2$ or $CH_2CHl$;

Z is H, Cl, CCl$_3$, —SO$_2$CH$_3$ or morpholinyl;
each W is independently H or Cl; and
at least one of T, Y and Z is chloromethyl and at least one of T, W, Y and Z is Cl;

said chloropyridine compound being antidotally active with said herbicide compound and wherein said chloropyridine compound is present in an effective amount ranging between about 0.01 to about 4 parts by weight of the chloropyridine compound per part of herbicide compound.

2. The composition as in claim 1 wherein the herbicidal compound is an S-alkyl dialkylthiocarbamate and T is Cl, Y is CCl$_3$ and Z and each W are each H.

3. The composition as in claim 1 wherein the herbicidal compound is 2-(2,2,2-trichloroethyl)-2-(3,5-dichlorophenyl)oxirane, T is Cl, Y is CCl$_3$ and Z and each W are each H.

4. The composition as in claim 1 wherein the chloropyridine compound is present in an effective amount ranging between about 0.1 to about 1 part by weight of the chloropyridine compound per part of herbicide compound.

5. The composition as in claim 2 which contains, additionally, the antidote compound R-25788 in an antidotal amount.

6. The composition as in claim 5 in which the S-alkyl dialkylthiocarbamate compound is butylate or EPTC.

7. The composition as in claim 2 which contains by weight from about 0.25 to about 3.75 percent of S-alkyl dialkylthiocarbamate compound and from about 0.25 to about 1.25 percent of the chloropyridine compound.

8. The composition as in claim 7 in which the chloropyridine compound is nitrapyrin.

9. The composition as in claim 7 which additionally contains about 0.25 to about 0.63 percent of R-25788.

10. The composition as in claim 9 in which the chloropyridine compound is nitrapyrin.

11. The composition as in claim 8 in the form of an emulsifiable concentrate composition.

12. The composition as in claim 10 in the form of an emulsifiable concentrate composition.

13. A method of protecting a plant crop from injury due to an active herbicidal compound selected from the group consisting of the herbicidal S-alkyl dialkylthiocarbamates wherein alkyl contains 2 to 6 carbons and is straight chained, branched or cyclic and 2-(2,2,2-trichloroethyl)-2-(3,5-dichlorophenyl)oxirane, comprising applying to the soil, in which a herbicidally effective amount of said active herbicidal compound is used, a non-phytotoxic antidotally effective amount of an antidote compound corresponding to the formula:

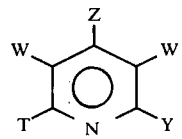

wherein:
T is H, Cl, CCl$_3$, CH$_2$Cl or CHCl$_2$;
Y is H, NH$_2$, Cl, CCl$_3$, CHCl$_2$ or CH$_2$Cl;
Z is H, Cl, CCl$_3$, —SO$_2$CH$_3$ or morpholinyl;
and each W is independently H or Cl;
said chloropyridine compound being antidotally active with said herbicide compound and wherein said chloropyridine compound is present in an effective amount ranging between about 0.01 to about 4 parts by weight of the chloropyridine compound per part of herbicide compound.

14. The method as in claim 13 wherein the active herbicidal compound is an S-alkyl dialkylthiocarbamate.

15. The method as in claim 14 wherein the herbicidal compound is applied at a herbicidally effective rate in the range of about 1 to 6 lb/acre and the antidote compound is applied at an antidotally effective rate in the range of about 0.2 to about 2 lb/acre.

16. The method as in claim 13 wherein the compounds are applied to the soil in the form of a composition according to claim 1.

17. The method as in claim 13 wherein the respective compounds are applied substantially concurrently at respectively different times.

18. The method as in claim 15 wherein the herbicidal compound and the antidote compound are applied to any of corn, cotton, soybeans, peanuts, sugar beets, dry beans or rice.

19. The method as in claim 15 wherein the antidote compound is nitrapyrin.

20. The method as in claim 13 wherein the compounds are applied in combination with R-25788 in the form of a composition as in claim 5.

21. The herbicidal method as in claim 13 wherein the active herbicidal compound is 2-(2,2,2-trichloroethyl)-2-(3,5-dichlorophenyl)oxirane.

22. The method as in claim 21 in which the oxirane compound is applied at a herbicidally effective rate in the range of about 0.5 to about 5 lb/acre and the antidote compound is applied at an antidotally effective rate in the range of about 0.2 to about 2 lb/acre.

23. The method as in claim 21 wherein the compounds are applied to the soil in the form of a composition according to claim 1.

24. The method as in claim 21 wherein the herbicidal compound and the antidote compound are applied to any of corn, sorghum, soybeans and rice.

25. The method as in claim 21 wherein the herbicidal compound is applied at a herbicidally effective rate in the range of about 2 to about 6 lb/acre and the antidote compound is applied at the rate of about 0.2 to about 2 lb/acre.

26. The method as in claim 21 wherein the antidote compound is nitrapyrin.

27. The method as in claim 24 wherein the antidote compound is nitrapyrin.

28. The method as in claim 13 wherein the respective compounds are applied simultaneously.

* * * * *

UNITED STATES PATENT AND TRADEMARK OFFICE
CERTIFICATE OF CORRECTION

PATENT NO. : 4,266,964

DATED : May 12, 1981

INVENTOR(S) : Theodore W. Holmsen, Norman H. Kurihara, Paul A. Thomas

It is certified that error appears in the above-identified patent and that said Letters Patent are hereby corrected as shown below:

Column 2, line 26 of the Abstract reading "dicloromethyl" should read -- dichloromethyl --.

Column 3, line 29, a comma should be added after the word used.

Column 4, line 32, reading "rops" should read -- crops --.

Column 4, line 55, reading "sobyeans" should read -- soybeans --.

Column 7, line 49, reading "applcation" should read -- application --.

UNITED STATES PATENT AND TRADEMARK OFFICE
CERTIFICATE OF CORRECTION

PATENT NO. : 4,266,964
DATED : May 12, 1981
INVENTOR(S) : Theodore W. Holmsen, Norman H. Kurihara, Paul A. Thomas It is certified that error appears in the above—identified patent and that said Letters Patent is hereby corrected as shown below:

Column 8, line 54 of Table IV the number "5" should read -- 0.5 --.

Column 10, line 57, reading "chlorpyri-" should read -- chloropyri- --.

Column 10, line 68, reading "CH1;" should read -- Cl; --.

Signed and Sealed this

Third Day of November 1981

[SEAL]

Attest:

GERALD J. MOSSINGHOFF

Attesting Officer    Commissioner of Patents and Trademarks